(12) United States Patent
Battista et al.

(10) Patent No.: US 12,268,605 B2
(45) Date of Patent: Apr. 8, 2025

(54) MOBILE BEARING PROSTHETIC IMPLANT SYSTEM

(71) Applicants: Lawrence Battista, Estero, FL (US);
Russell P Becket, Fort Myers, FL (US);
Lorenzo N Battista, Estero, FL (US);
Jacob D Grate, Asheville, NC (US)

(72) Inventors: Lawrence Battista, Estero, FL (US);
Russell P Becket, Fort Myers, FL (US);
Lorenzo N Battista, Estero, FL (US);
Jacob D Grate, Asheville, NC (US)

(*) Notice: Subject to any disclaimer, the term of this patent is extended or adjusted under 35 U.S.C. 154(b) by 208 days.

(21) Appl. No.: 17/399,781

(22) Filed: Aug. 11, 2021

(65) Prior Publication Data
US 2023/0048455 A1 Feb. 16, 2023

(51) Int. Cl.
A61F 2/28 (2006.01)
A61F 2/30 (2006.01)
A61L 27/06 (2006.01)
A61L 27/18 (2006.01)

(52) U.S. Cl.
CPC ............ *A61F 2/2803* (2013.01); *A61L 27/06* (2013.01); *A61L 27/18* (2013.01); *A61F 2002/30224* (2013.01); *A61F 2002/30242* (2013.01); *A61F 2002/30428* (2013.01); *A61F 2002/30538* (2013.01); *A61F 2002/30639* (2013.01); *A61F 2310/00023* (2013.01); *A61L 2430/02* (2013.01)

(58) Field of Classification Search
CPC .......... A61F 2/3099; A61F 2002/30991; A61F 2002/30428; A61F 2002/30654; A61F 2002/30655; A61F 2002/538; A61F 2/2803; A61F 2002/30993
See application file for complete search history.

(56) References Cited

U.S. PATENT DOCUMENTS

| | | | | |
|---|---|---|---|---|
| 4,778,472 A | * | 10/1988 | Homsy | A61F 2/3099 |
| | | | | 623/17.17 |
| 5,549,680 A | * | 8/1996 | Gordon | A61F 2/3099 |
| | | | | 623/17.17 |
| 6,132,466 A | * | 10/2000 | Hoffman | A61F 2/3099 |
| | | | | 623/17.17 |

(Continued)

FOREIGN PATENT DOCUMENTS

| | | | | |
|---|---|---|---|---|
| CN | 106562842 A | * | 4/2017 | ........... A61F 2/3099 |
| CN | 207125817 U | * | 3/2018 | ........... A61F 2/3099 |

(Continued)

*Primary Examiner* — Javier G Blanco
(74) *Attorney, Agent, or Firm* — The Rapacke Law Group, P.A.; Andrew Rapacke

(57) ABSTRACT

A mobile bearing prosthetic implant may include a fossa implant seated in the fossa cavity of the skull and secured to the zygomatic arch. The fossa implant may define a primary recess constructed and arranged to mimic the articular eminence of the temporal bone such that a floating bearing connected to a ramus implant may translate along the original path that the condylar head would take during movement of the jaw. The floating bearing may be constructed and arranged to move from the first jaw angle recess to the second jaw angle recess and is positionable therebetween such that a longitudinal axis of the floating bearing is perpendicular to the direction of movement of the floating bearing within the fossa implant.

4 Claims, 5 Drawing Sheets

(56) References Cited

U.S. PATENT DOCUMENTS

| | | | |
|---|---|---|---|
| 2015/0182340 A1* | 7/2015 | Ramos | A61F 2/3099 623/17.17 |
| 2016/0081806 A1* | 3/2016 | Dubois | A61F 2/4603 623/17.17 |
| 2017/0100252 A1* | 4/2017 | Pendola | A61F 2/3099 |
| 2020/0129296 A1* | 4/2020 | Chary | A61F 2/30942 |
| 2022/0409377 A1* | 12/2022 | Dimitroulis | A61F 2/3099 |

FOREIGN PATENT DOCUMENTS

| | | | | |
|---|---|---|---|---|
| EP | 0628293 A1 * | 12/1994 | | A61F 2/3099 |
| EP | 3656357 B1 * | 8/2021 | | A61B 17/15 |
| FR | 2558721 A1 * | 8/1985 | | A61F 2/3099 |
| JP | 11146889 A * | 6/1999 | | A61F 2/3099 |
| WO | WO-2008061769 A2 * | 5/2008 | | A61F 2/3099 |
| WO | WO-2016014006 A1 * | 1/2016 | | A61F 2/3099 |
| WO | WO-2017075664 A1 * | 5/2017 | | A61F 2/3099 |

* cited by examiner

MOBILE BEARING PROSTHETIC IMPLANT SYSTEM

TECHNICAL FIELD

The embodiments generally relate to implants for the temporomandibular joint (TMJ) in a jaw.

BACKGROUND

A TMJ implant may include a fossa implant, a bearing, and a ramus implant. Fossa implants and ramus implants may be used to replace the TMJ in a jaw and may require custom manufacturing to best suit a recipient. The fossa implant may require custom design and manufacture to fit a recipients fossa cavity and zygomatic arch. The bearing, or means by which the fossa implant is connected to the ramus implant, may require custom design and manufacture to achieve proper movement of the implant in use.

SUMMARY

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

A mobile bearing prosthetic implant system may be designed for the replacement of the TMJ. The prosthetic may include a fossa implant, at least one bearing, and a ramus implant. The prosthetic allows for a first bearing articulation inside a larger second bearing designed to translate in a medial-lateral direction as well as an anterior-posterior direction, thereby minimizing wear and reproducing normal movement of the joint. The prosthetic allows for a floating bearing arrangement to further minimize wear and reproduce normal movement of the TMJ. The prosthetic may consist of a ball and socket joint that may utilize a snap fit bearing or barrel arrangement which may be made of cobalt chrome, titanium alloys, stainless steel, ultra-high molecular weight polyethylene (UHMWPE), high density polyethylene (HDPE), polyetheretherketone (PEEK), or other ceramic materials and articulations coupled with ultra-high molecular weight polyethylene. A ball portion extending into a poly component may be a spherical, elliptical, barrel, or other shaped element. The articulating surfaces of the poly component could have a round, elliptical, or other shape to provide a natural movement of the prosthetic components. The ramus implant may be fixated with screws and have a slight anatomical bend in order to facilitate proper articulation with the poly bearing. The fossa component may also be fixated with screws as well as incorporating a biological fixation. The prosthetic may be constructed and arranged such that fossa implants and ramus implants need not be custom manufactured to best suit a recipient and instead may provide for an "off the shelf" solution.

Other illustrative variations within the scope of the invention will become apparent from the detailed description provided hereinafter. The detailed description and enumerated variations, while disclosing optional variations, are intended for purposes of illustration only and are not intended to limit the scope of the invention.

BRIEF DESCRIPTION OF THE DRAWINGS

A complete understanding of the present embodiments and the advantages and features thereof will be more readily understood by reference to the following detailed description when considered in conjunction with the accompanying drawings wherein.

DETAILED DESCRIPTION

Figure 1:
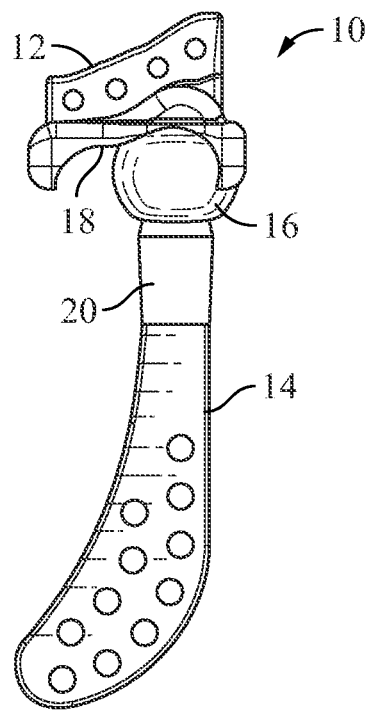
FIG. 1 illustrates a side view of a mobile bearing prosthetic implant system according to some variations described herein.

The specific details of the single embodiment or variety of embodiments described herein are to the described system and methods of use. Any specific details of the embodiments are used for demonstration purposes only and no unnecessary limitations or inferences are to be understood from there.

It is noted that the embodiments reside primarily in combinations of components and procedures related to the system. Accordingly, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Temporomandibular disorder (TMD) is a broad classification of disorders of the jaw muscles, TMJ, and the mandibular nerves. The disorder may include any problem that results in the system of muscles, bones, and joints associated with the jaw that prevents proper functionality. Due to varying causes, TMD can have a wide range of discomfort and symptoms, with the common symptoms consisting of jaw soreness, headaches, earaches, jaw clicking, locking of the jaw, limited mouth motion, teeth clenching, dizziness, sensitive teeth, tingling sensation in the fingers, and a change in how the upper and lower set of teeth fit together. If the articular disk is pushed past the articular eminence of the temporal bone, surgery is typically required to repair the joint. In the case of degenerative diseases, total joint replacement may be one of the only options, as the bone and surrounding tissue is damaged to the point where functionality is not salvageable in the absence of artificial replacements.

A mobile bearing prosthetic implant may include a fossa implant seated in the fossa cavity of the skull and secured to the zygomatic arch. The fossa implant may define a primary recess constructed and arranged to mimic the articular eminence of the temporal bone such that a floating bearing may translate along the original path that the condylar head would take during movement of the jaw. The primary recess may include a first jaw angle recess and second jaw angle recess wherein the first jaw angle recess is constructed and arranged to position a jaw at a 0-degree jaw angle accounting for closed jaw offset. The second jaw angle recess may be constructed and arranged to position a jaw at a 25-degree jaw angle accounting for closed jaw offset. The floating bearing may be constructed and arranged to move from the first jaw angle recess to the second jaw angle recess and is positionable therebetween such that a longitudinal axis of the floating bearing is perpendicular to the direction of movement of the floating bearing within the fossa implant. The fossa implant may be made of cobalt chrome, titanium alloys, stainless steel, UHMWPE, HDPE, PEEK, or other materials.

A ramus implant may be secured to the ramus of the mandible and may include a floating bearing constructed and arranged to travel within the primary recess such that natural movement of the jaw may be accomplished via the mobile bearing prosthetic implant. The ramus implant may include a first bearing on to which the floating bearing may snap fit. The ramus implant may include a plate which may be secured to bone. The plate may extend into an offset stem, neck, and first bearing. The stem, neck, and first bearing may be aligned approximately in a plane parallel to, but spaced from, a plane defined by the plate. The stem may be generally cylindrical and may extend into a tapered neck which may be attached to an approximately spherical first bearing. The ramus implant may be made of cobalt chrome, titanium alloys, stainless steel, UHMWPE, HDPE, PEEK, or other materials.

The floating bearing may snap fit onto the first bearing and may generally spherocylindrical in shape i.e. "capsule" like in shape including a primarily cylindrical center portion and two, semi-spherical ends opposite one another. The floating bearing may be made of cobalt chrome, titanium alloys, stainless steel, UHMWPE, HDPE, PEEK, or other materials.

Figure 2:
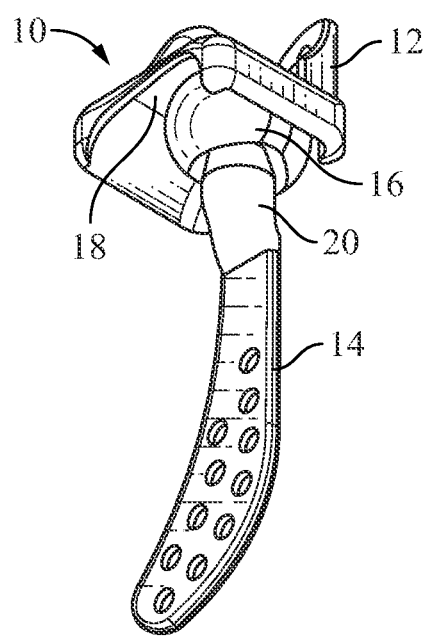
FIG. 2 illustrates a perspective view of a mobile bearing prosthetic implant system according to some variations described herein.
Figure 8A:
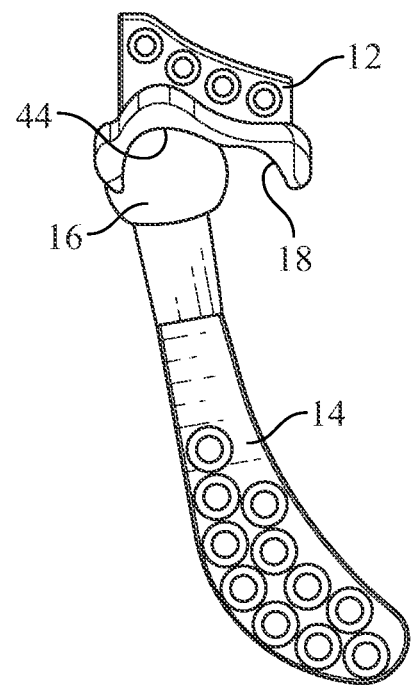
FIGS. 8a and 8b illustrate a view of a mobile bearing prosthetic implant system according to some variations described herein.
Figure 8B:
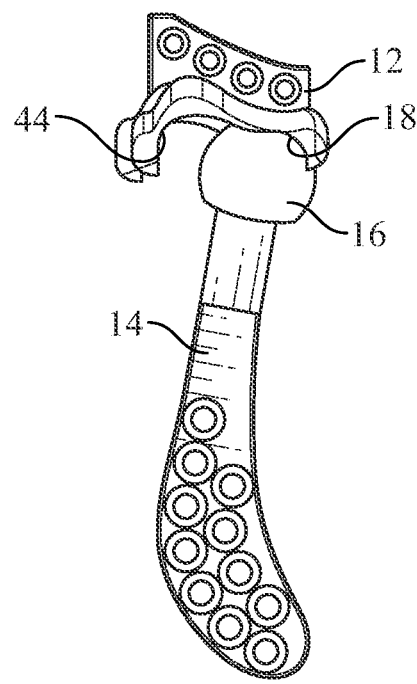

FIGS. 1 and 2 illustrate one variation of a mobile bearing prosthetic implant 10. A prosthetic implant 10 may include a fossa implant 12, a ramus implant 14, and a floating bearing 16. The fossa implant 12 may define a primary recess 18 in which the floating bearing 16 may be movably seated. The ramus implant 14 may include a stem and a tapered neck extending to a first bearing (not shown) on to which the floating bearing 16 may be connected. The primary recess 18 may be constructed and arranged to allow the floating bearing 16 to travel therein while the prosthetic implant 10 is in use, as best shown in FIGS. 8a and 8b. In use, the fossa implant 12 may be secured to the bone of a patient, and in particular to the zygomatic arch. The ramus implant 14 may be secured to the bone of a patient, and in particular to the ramus of the mandible. A patient may utilize the prosthetic implant 10 as the primary hinge upon which the mandible pivots during speaking, chewing, and the like. In use, the floating bearing 16 may travel within the primary recess 18 and pivot within the primary recess 18 such that the mandible may move naturally.

Figure 3:
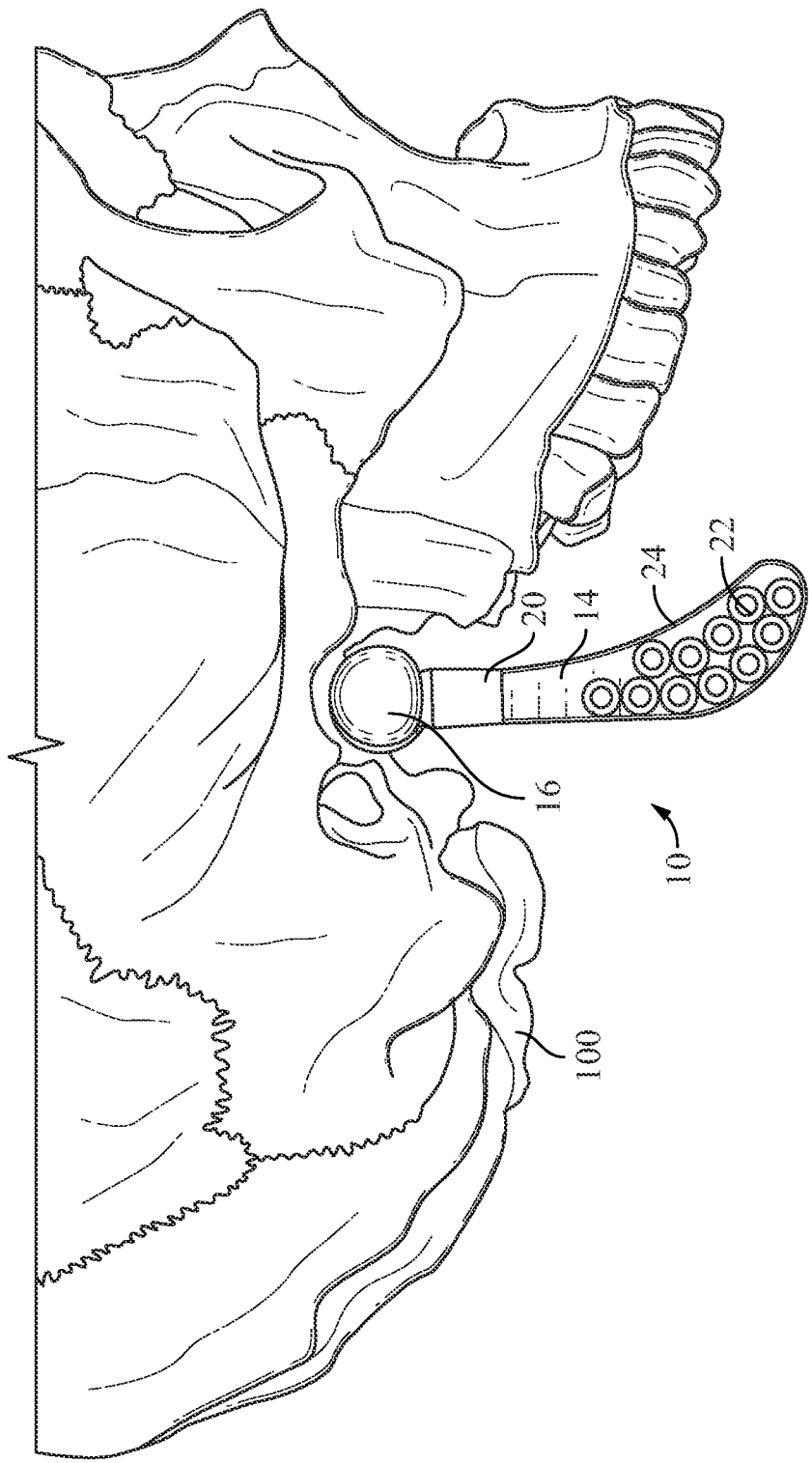
FIG. 3 illustrates a view of a portion of a mobile bearing prosthetic implant system according to some variations described herein.

FIG. 3 illustrates a perspective view of a mobile bearing prosthetic implant 10 positioned in a skull 100. For the purpose of visibility, FIG. 3 does not depict the fossa implant 12 in which the floating bearing 16 may be movably seated. The ramus implant 14 may include an offset stem 20 protruding from the plate and transitioning into a neck upon which a first bearing may be affixed. The floating bearing 16 may be positioned on the first bearing and may be a snap fitted. The ramus implant 14 may define a first plurality of countersunk through holes 22 that may be constructed and arranged to facilitate the attachment of the ramus implant 14 to bone. The ramus implant 14 may define a curved perimeter 24 constructed and arranged to mimic the approximate shape of portions of the ramus, mandibular foramen, and body of a mandible. The ramus implant 14 may define a curved perimeter 24 constructed and arranged to mimic the angle at which the ramus attaches to the body of the jaw. The ramus implant 14 may further facilitate the attachment of the ramus implant 14 to bone such as the mandible.

Figure 4:
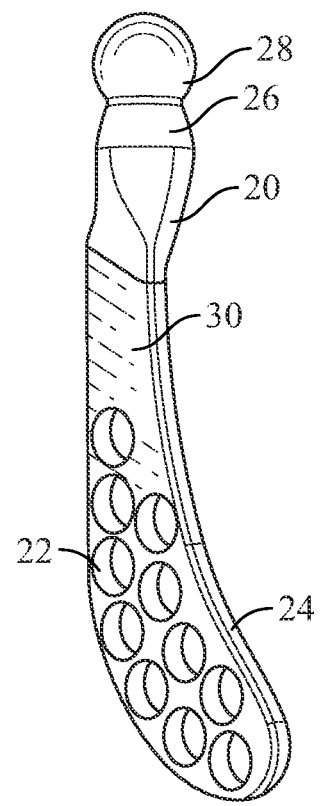
FIG. 4 illustrates a view of a portion of a mobile bearing prosthetic implant system according to some variations described herein.

FIG. 4 illustrates a perspective view of a ramus implant as part of a mobile bearing prosthetic implant system. The ramus implant may include a plate portion 30 connected to and offset from a stem 20 which may transition into a tapered neck 26 which may be affixed to the first bearing 28. At least a portion of the stem 20, neck 26, and first bearing 28 may be offset from the plate 30 such that stem 20, neck 26, and first bearing 28 may receive downward force in a plane parallel to that of a plane defined by the plate 30. The ramus implant 14 may define a first plurality of countersunk through holes 22 that may be constructed and arranged to facilitate the attachment of the ramus implant 14 to bone. The ramus implant 14 may define a perimeter 24 constructed and arranged to further facilitate the attachment of the ramus implant 14 to bone, and in particular, the mandible.

Figure 5:
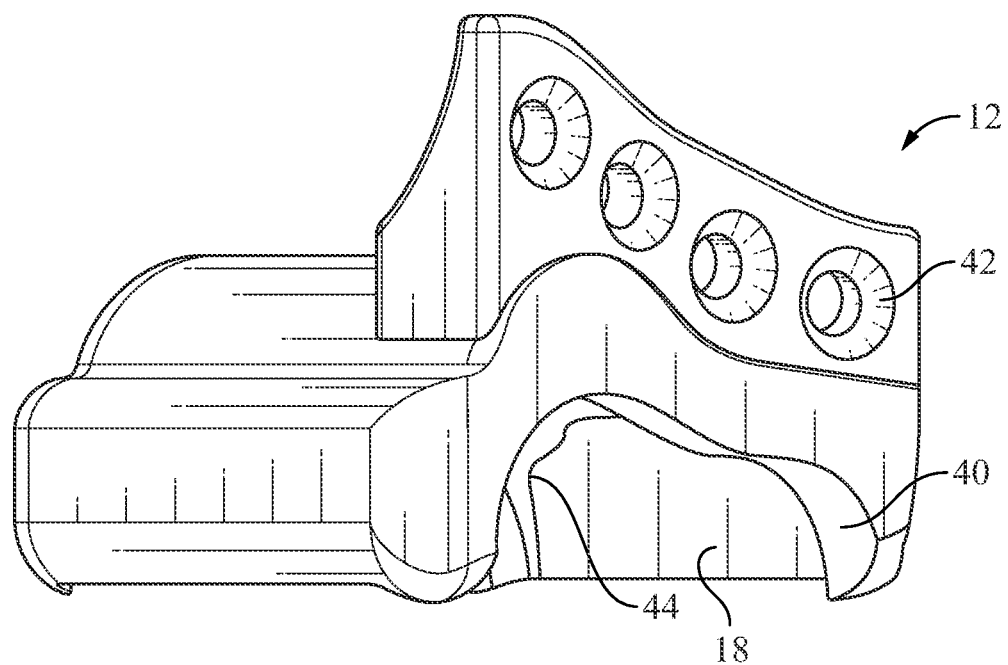
FIG. 5 illustrates a view of a portion of a mobile bearing prosthetic implant system according to some variations described herein.
Figure 6:
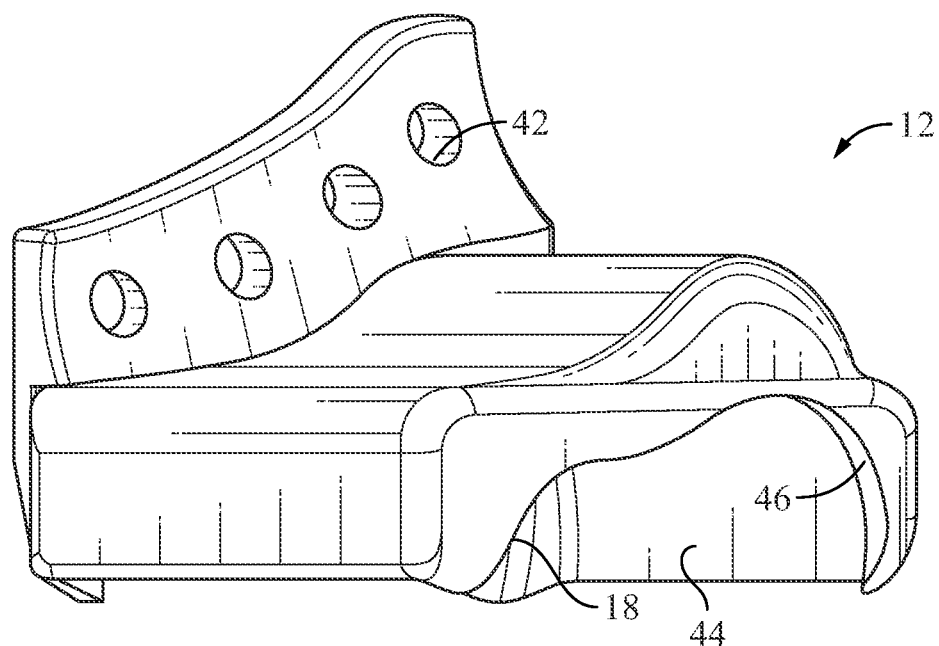
FIG. 6 illustrates a view of a portion of a mobile bearing prosthetic implant system according to some variations described herein.

FIGS. 5 and 6 illustrate views of fossa implant as part of a mobile bearing prosthetic implant. The fossa implant 12 may find a primary recess 18 that may include a first jaw angle recess 46 and a second jaw angle recess 44. The first jaw angle recess 46 and second jaw angle recess 44 make up a continuous primary recess 18. The primary recess 18, first jaw angle recess 46, and second jaw angle recess 44 may be constructed and arranged to allow the ramus implant and floating bearing to mimic the natural movement of the jaw by allowing the floating bearing to travel therein. The primary recess 18, first jaw angle recess 46, and second jaw angle recess 44 may be constructed and arranged to mimic the natural anatomy of the articular eminence of the temporal bone that a condylar head of the ramus would translate over during movement of the jaw. The fossa implant 12 may further define a first floating bearing profile 40 and second floating bearing profile 48 constructed and arranged to partially mimic the articular eminence of the temporal bone and the profile of the primary recess 18 while also allowing a portion of the floating bearing to extend outside of a portion of the fossa implant. The fossa implant may further define a second plurality of countersunk through holes 42 constructed and arranged to facilitate the attachment of the fossa implant to bone.

Figure 7A:
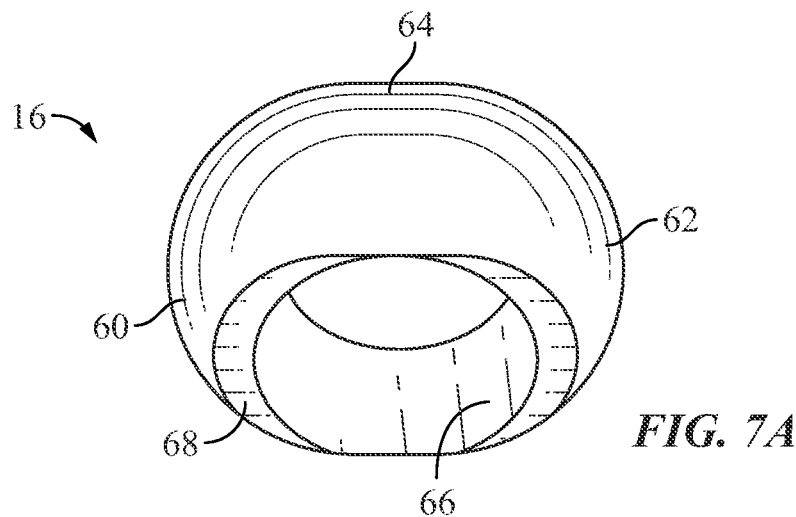
FIGS. 7a and 7b illustrate a view of a portion of a mobile bearing prosthetic implant system according to some variations described herein.
Figure 7B:
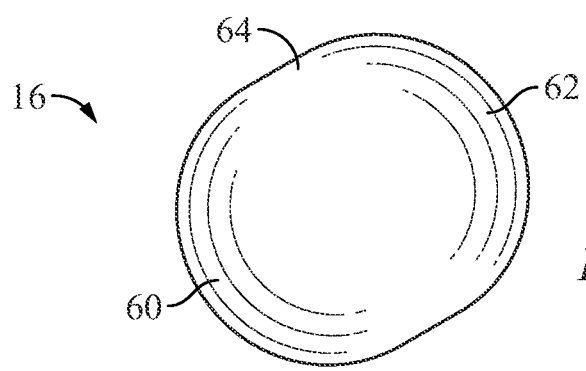

FIGS. 7a and 7b illustrate variations of a floating bearing as part of a mobile bearing prosthetic implant system. The floating bearing 16 may be generally spherocylindrical in shape including a generally cylindrical portion 64 disposed between a first semi spherical portion 60 opposite a second semi spherical portion 62. The floating bearing 16 may define a generally spherical recess 66 constructed and arranged to mechanically engage with the first bearing of the ramus implant. The floating bearing 16 may further define a face 68 constructed and arranged to further facilitate attachment of the floating bearing 16 to the first bearing. The floating bearing 16 may be snap fit to the first bearing.

FIGS. 8a and 8b illustrate a view of a mobile bearing prosthetic implant system including a fossa implant 12, a ramus implant 14, and a floating bearing 16 seated in the primary recess 18. FIG. 8a depicts the floating bearing 16 positioned in the second jaw angle recess 44 constructed and arranged to position the prosthetic implant add a zero-degree jaw angle accounting for a closed jaw offset of 10 degrees. FIG. 8b depicts the floating bearing 16 positioned in the first jaw angle recess 46 constructed and arranged to position the prosthetic implant at a 25-degree jaw angle accounting for a closed jaw offset of 10 degrees. The floating bearing 16 may be constructed and arranged to travel within the primary recess 18 between the first jaw angle recess 46 in the second jaw angle recess 44 to mimic the natural movement of the jaw. The primary recess 18 may be constructed and arranged to mimic the natural anatomy of the articular eminence of the temporal bone that a condylar head of the ramus would translate over during movement of the jaw.

The following description of variants is only illustrative of components, elements, acts, products, and methods considered to be within the scope of the invention and are not in any way intended to limit such scope by what is specifically disclosed or not expressly set forth. The components, elements, acts, products, and methods as described herein may be combined and rearranged other than as expressly described herein and are still considered to be within the scope of the invention.

According to variation 1, mobile bearing prosthetic implant may include a fossa implant defining a first jaw angle recess and a second jaw angle recess constructed and arranged to receive a floating bearing therein; a ramus implant including a ramus plate, a stem, a neck, and a first bearing; and a floating bearing snap-fit onto the first bearing wherein the floating bearing is constructed and arranged to move from the first jaw angle recess to the second jaw angle recess and is positionable therebetween.

Variation 2 may include a mobile bearing prosthetic implant as in variation 1, wherein the first bearing is approximately spherical in shape.

Variation 3 may include a mobile bearing prosthetic implant as in any of variations 1 through 2, wherein the floating bearing is approximately spherocylindrical in shape.

Variation 4 may include a mobile bearing prosthetic implant as in any of variations 1 through 3, wherein the floating bearing defines a spherical recess therein constructed and arranged to snap-fit the floating bearing onto the first bearing.

Variation 5 may include a mobile bearing prosthetic implant as in any of variations 1 through 4, wherein the floating bearing is approximately spherocylindrical in shape is constructed and arranged to move from the first jaw angle recess to the second jaw angle recess and is positionable therebetween such that a longitudinal axis of the floating bearing is perpendicular to the direction of movement within the fossa implant.

Variation 6 may include a mobile bearing prosthetic implant as in any of variations 1 through 5, wherein the fossa implant includes Ti-6Al-4V.

Variation 7 may include a mobile bearing prosthetic implant as in any of variations 1 through 6, wherein the ramus implant includes Ti-6Al-4V Variation 8 may include a mobile bearing prosthetic implant as in any of variations 1 through 7, wherein the floating bearing includes polyetheretherketone.

Variation 9 may include a mobile bearing prosthetic implant as in any of variations 1 through 9, wherein the first jaw angle recess is constructed and arranged to position a jaw at a 0-degree jaw angle accounting for closed jaw offset.

Variation 10 may include a mobile bearing prosthetic implant as in any of variations 1 through 9, wherein the second jaw angle recess is constructed and arranged to position a jaw at a 25-degree jaw angle accounting for closed jaw offset.

Variation 11 may include a mobile bearing prosthetic implant as in any of variations 1 through 10, wherein the fossa implant defines a first plurality of countersunk recesses constructed and arrange to facilitate securing the fossa implant to bone.

Variation 12 may include a mobile bearing prosthetic implant as in any of variations 1 through 11, wherein the ramus implant defines a second plurality of countersunk recesses constructed and arrange to facilitate securing the fossa implant to bone.

Variation 13 may include a mobile bearing prosthetic implant as in any of variations 1 through 12, wherein the stem, neck, and first bearing are at least partially offset from ramus plate in a plane approximately parallel to that of the ramus plate.

According to variation 14, a mobile bearing prosthetic implant may include a fossa implant including Ti-6Al-4V and defining a first jaw angle recess and a second jaw angle recess constructed and arranged to receive a floating bearing therein; a ramus implant including Ti-6Al-4V and a ramus plate, a stem, a neck, and an approximately spherical first bearing, the stem, neck, and first bearing being at least partially offset from ramus plate in a plane parallel to that of the ramus plate; and an approximately spherocylindrical floating bearing including polyetheretherketone snap-fit onto the first bearing wherein the floating bearing is constructed and arranged to move from the first jaw angle recess to the second jaw angle recess and is positionable therebetween.

Variation 15 may include a mobile bearing prosthetic implant as in variation 14, wherein the floating bearing is approximately spherocylindrical in shape is constructed and arranged to move from the first jaw angle recess to the second jaw angle recess and is positionable therebetween such that a longitudinal axis of the floating bearing is perpendicular to the direction of movement of the floating bearing within the fossa implant.

Variation 16 may include a mobile bearing prosthetic implant as in any of variations 14 through 15, wherein the first jaw angle recess is constructed and arranged to position a jaw at a 0-degree jaw angle accounting for closed jaw offset.

Variation 17 may include a mobile bearing prosthetic implant as in any of variations 15 through 16, wherein the second jaw angle recess is constructed and arranged to position a jaw at a 25-degree jaw angle accounting for closed jaw offset.

Variation 18 may include a mobile bearing prosthetic implant as in any of variations 14 through 17, wherein the stem, neck, and first bearing are at least partially offset from ramus plate in a plane approximately parallel to that of the ramus plate According to variation 19, a mobile bearing prosthetic implant may include a fossa implant comprising Ti-6Al-4V and defining a first jaw angle recess and a second jaw angle recess constructed and arranged to mimic the natural anatomy of the articular eminence of the temporal bone and receive a floating bearing therein; a ramus implant including Ti-6Al-4V and a ramus plate, a stem, a neck, and an approximately spherical first bearing, the stem, neck, and first bearing being at least partially offset from ramus plate in a plane parallel to that of the ramus plate; and an approximately spherocylindrical floating bearing including polyetheretherketone snap-fit onto the first bearing wherein the floating bearing is constructed and arranged to move from the first jaw angle recess to the second jaw angle recess and is positionable therebetween such that a longitudinal axis of the floating bearing is perpendicular to the direction of movement of the floating bearing within the fossa implant such that a jaw is positionable between a 0-degree jaw angle and a 25-degree jaw angle accounting for closed jaw offset.

Variation 20 may include a mobile bearing prosthetic implant as in variation 19 wherein the stem, neck, and first bearing are at least partially offset from ramus plate in a plane approximately parallel to that of the ramus plate.

Many different embodiments have been disclosed herein, in connection with the above description and the drawing. It will be understood that it would be unduly repetitious and obfuscating to describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for anyone of the elements in the claims below or that a single element can be substituted for two or more elements in a claim. Although elements can be described above as acting in certain combinations, and even initially claimed as such, it is to be expressly understood that one or more elements from a claimed combination can, in some cases, be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible considering the above teachings without departing from the following claims.

What is claimed is:

1. A temporomandibular joint implant, comprising:
    a fossa implant comprising a first jaw angle recess and a second jaw angle recess constructed and arranged to mimic the natural anatomy of the articular eminence of the temporal bone and sized and configured to receive a floating bearing therein;
    a ramus implant comprising a ramus plate, a stem extending from the ramus plate, a tapered neck extending from the stem, and a spherical bearing extending from the tapered neck, wherein the stem, the tapered neck, and the spherical bearing being at least partially offset from the ramus plate in a plane parallel to that of the ramus plate; and
    a spherocylindrical floating bearing snap-fit onto the spherical bearing of the ramus implant, wherein the spherocylindrical floating bearing is sized and configured to move from the first jaw angle recess to the second jaw angle recess,
    wherein the fossa implant comprises Ti-6Al-4V, wherein the ramus implant comprises Ti-6Al-4V, and wherein the spherocylindrical floating bearing comprises polyetheretherketone (PEEK),
    wherein a longitudinal axis of the spherocylindrical floating bearing is perpendicular to the direction of movement of the spherocylindrical floating bearing within the fossa implant,
    wherein the first jaw angle recess is constructed and arranged to position a jaw at a 0-degree jaw angle accounting for closed jaw offset,
    wherein the second jaw angle recess is constructed and arranged to position a jaw at a 25-degree jaw angle accounting for closed jaw offset,
    wherein the first jaw angle recess defines a first floating bearing profile, wherein the second jaw angle recess defines a second floating bearing profile, and wherein the first floating bearing profile is different from the second floating bearing profile, and
    wherein the first jaw angle recess and the second jaw angle recess are configured to allow the ramus implant and the spherocylindrical floating bearing to mimic natural movements of a jaw by allowing the movement of the spherocylindrical floating bearing.

2. The temporomandibular joint implant as in claim 1, wherein the spherocylindrical floating bearing defines a spherical recess therein constructed and arranged to snap-fit the spherocylindrical floating bearing onto the spherical bearing of the ramus implant.

3. The temporomandibular joint implant as in claim 1, wherein the fossa implant defines a first plurality of counter-sunk recesses constructed and arrange to facilitate securing the fossa implant to bone.

4. The temporomandibular joint implant as in claim 1, wherein the ramus implant defines a second plurality of counter-sunk recesses constructed and arrange to facilitate securing the ramus implant to bone.

* * * * *